(12) United States Patent
Masaoka et al.

(10) Patent No.: US 7,425,300 B2
(45) Date of Patent: Sep. 16, 2008

(54) METHOD FOR STERILIZING PACKAGING MATERIAL BY USING HIGH VOLTAGE PULSE POWER SOURCE

(75) Inventors: Satoshi Masaoka, Tokyo (JP); Hideo Hasegawa, Osaka-fu (JP)

(73) Assignees: Dai Nippon Printing Co., Ltd., Tokyo (JP); Sanyo Electric Co., Ltd., Osaka-fu (JP)

( * ) Notice: Subject to any disclaimer, the term of this patent is extended or adjusted under 35 U.S.C. 154(b) by 731 days.

(21) Appl. No.: 10/601,007

(22) Filed: Jun. 20, 2003

(65) Prior Publication Data

US 2004/0047762 A1  Mar. 11, 2004

(30) Foreign Application Priority Data

Jun. 21, 2002  (JP) .............................. 2002-181794

(51) Int. Cl.
*A61L 2/14* (2006.01)
(52) U.S. Cl. ................. 422/22; 422/186.04; 422/28
(58) Field of Classification Search ............... 422/22, 422/23, 186.04, 186.05
See application file for complete search history.

(56) References Cited

U.S. PATENT DOCUMENTS

| | | | | |
|---|---|---|---|---|
| 3,383,163 A | * | 5/1968 | Menashi | 422/23 |
| 3,466,850 A | | 9/1969 | Hudson et al. | 53/28 |
| 3,701,628 A | | 10/1972 | Ashman et al. | |
| 3,819,985 A | * | 6/1974 | Dusevoir | 96/88 |
| 4,680,163 A | * | 7/1987 | Blidschun et al. | 422/28 |
| 5,084,239 A | | 1/1992 | Moulton et al. | 422/22 |
| 5,521,351 A | | 5/1996 | Mahoney | 219/121.59 |
| 6,103,190 A | * | 8/2000 | Tanimura et al. | 422/29 |
| 2002/0063537 A1 | * | 5/2002 | Nam et al. | 315/169.4 |
| 2004/0037736 A1 | * | 2/2004 | Perruchot et al. | 422/22 |

FOREIGN PATENT DOCUMENTS

| | | | |
|---|---|---|---|
| GB | 1098693 | | 1/1968 |
| JP | 8-168516 A | | 7/1996 |
| JP | 9-099922 A | | 4/1997 |
| WO | WO 97/22369 | * | 6/1997 |
| WO | WO 98 51608 | | 11/1998 |

* cited by examiner

*Primary Examiner*—Jill Warden
*Assistant Examiner*—Sean Conley
(74) *Attorney, Agent, or Firm*—Weingarten, Schurgin, Gagnebin & Lebovivi LLP (57) ABSTRACT

To provide a method for sterilizing a packaging material and a sterilizer used therefor, which do not cause unevenness in the sterilization effect, and uses high voltage pulses permitting to improve the sterilization effect. The purpose can be achieved by using such a discharge side electrode as is provided with unevenness having continuous projections on the discharge side surface, in the method in which the sterilizer is provided with a power source for generating high voltage, a discharge side electrode to which the high voltage generated by the power source is applied, and a ground side electrode arranged so as to be opposed to the discharge side of the discharge side electrode, and sterilizes a packaging material to be sterilized by placing it between both electrodes under normal temperature and normal pressure, and applying the high voltage pulses thereto in a gas atmosphere.

9 Claims, 4 Drawing Sheets

METHOD FOR STERILIZING PACKAGING MATERIAL BY USING HIGH VOLTAGE PULSE POWER SOURCE

BACKGROUND OF THE INVENTION

1. Field of the Invention

The present invention relates to a method for sterilizing packaging materials by using high voltage pulses power source and a device therefore. More specifically, it relates a method for sterilizing packaging materials for packaging materials such as liquids, solid bodies, or combinations of them such as foods, medical supplies, Chinese medicines, cosmetics, feeds, and fertilizers, especially, and to a method for sterilizing packaging materials for packaging foods by using high voltage pulses and a device thereof.

2. Detailed Description of the Related Art

Conventionally, as methods for sterilizing the packaging materials, reagent sterilization using an aqueous solution of peroxide, gas sterilization using ethylene oxide, ultraviolet sterilization, heat sterilization, or the like have been carried out in general. Moreover, many methods of sterilization (under vacuum or under normal pressure) using plasma classified as the same technology as this invention have been disclosed in the patent publications.

However, the reagent sterilization has a problem that sterilization reagent remain in the packaging materials after sterilization and the residues affect on quality of an article; the gas sterilization has also problems of remaining gas, a poor efficiency caused by batch processing, and a bad influence on quality of an article; the ultraviolet sterilization has also a problem that the sterilization effect is insufficient, especially, ineffective to molds; the heat sterilization is in danger of exerting thermal deformation and thermal contraction on plastic packaging materials, and use of a heat resistant packaging material to suppress the thermal deformation and thermal contraction increases costs; the sterilization by plasma under vacuum has a problem of making a system expensive and also having a poor efficiency due to batch processing; and in the sterilization by plasma under normal pressure using an Rf power source, an electrode gap needs to be a few millimeters or less, therefore, objects for sterilization are restricted to those of a flat form like a film, and the sterilization effect has also been insufficient.

For the above reason, methods for sterilizing packaging materials (for example, plastic containers, paper containers, glass containers, films, sheets, or the like) without using germicides, moreover, without heating are under development. One of the sterilization methods uses high voltage pulses, for example, the sterilization method is provided the system with a power source for generating high voltage, a discharge side electrode for applying thereto the high voltage generated by the power source, and a ground side electrode placed to be opposed to the discharge side electrode. By this method, the object is sterilized by placing a packaging material as an object for sterilization between both electrodes at normal temperature and under normal pressure, and applying the high voltage pulses across the electrodes.

Figure 9:
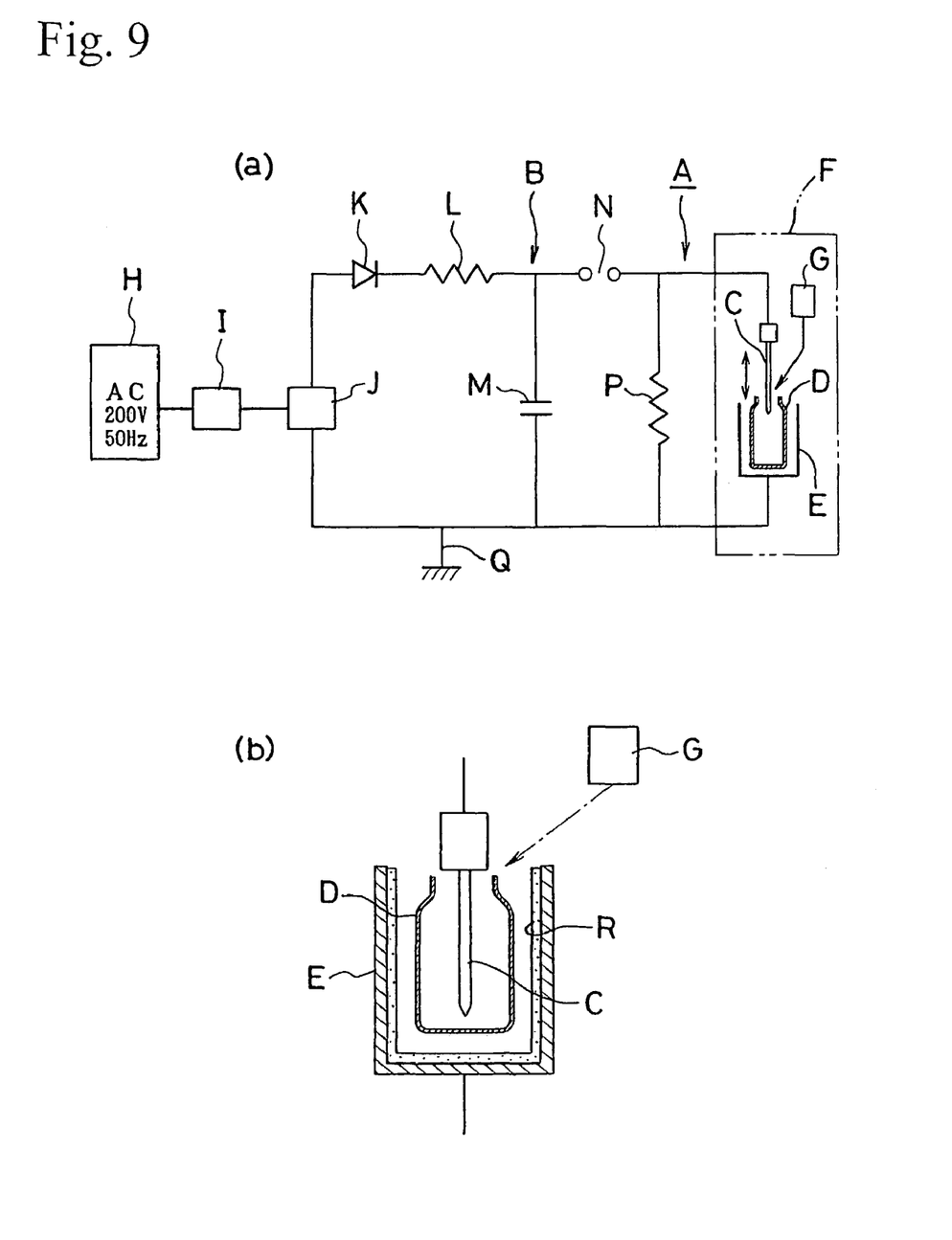
FIG. 9 shows a conventional example, in which (a) is a general configuration view of the sterilizer using high voltage pulses, and (b) is an enlarged schematic cross sectional view showing a part of the (a).

As an embodiment of a conventional high voltage pulse sterilization method, for example, as shown in FIG. 9-(a), a sterilizer A for containers is provided with a processing device comprising a power source B for generating high voltage, a discharge side electrode C for applying the high voltage generated by this power source B, a entrance and exit means (not illustrated) for putting this discharge side electrode C in and out of a packaging container D such as a PET bottle, and a ground side electrode E placed outside of the packaging container D, and is also provided with a gas supply means G for supplying a rare gas such as argon and helium into the packaging container D.

Moreover, the above-described power source B steps up the voltage inputted from the power source H through a Slidac I and a high voltage transformer J, and rectifies it by a full-wave rectification bridge K. Thereafter, the current value is decreased through a resistor L and a capacitor M is charged. The electric energy charged in the capacitor M is instantaneously discharged through a gap N, and is applied as a pulse voltage across the discharge side electrode C of the processing device F and the ground side electrode E, to sterilize a packaging material D by plasma generated by the high voltage pulses. In the figure, P is the resistor, and Q is the ground. Here, when a rare gas such as argon is supplied during discharge as shown in FIG. 9(b), breakdown voltage can be lowered, the plasma can be uniformly generated by the high voltage pulses, and favorable sterilization can be performed. Here, R is a dielectric provided inside of the ground side electrode E.

According to the above-described conventional high voltage pulse sterilization method, for example, in the case that the packaging material is a PET bottle or the like, the sterilization effect has been only about 1 to 2D [sterilization effect value D=−log (the survival number of bacteria/the initial number of bacteria)], and the sterilization has not been performed uniformly, and a practical sterilization effect has not been obtained.

The zealous studies repeated by the applicants of the present invention to solve the above problem have shown that the non-uniformity of the sterilization has been caused by the configuration that the discharge side electrode is in a shape of a round bar; strong high voltage pulse discharges are generated from the tip; and the strong high voltage pulse discharges are not effectively generated from the external wall of the round bar shape discharge side electrode, and the applicants have resulted in this invention.

Therefore, the first purpose of the present invention is to provide a method for sterilizing a packaging material by using high voltage pulses, in which non-uniformity is not caused to the sterilization effect and high voltage pulses are used in order to improve the sterilization effect, and the second purpose is to provide a sterilizer to be used therefor.

SUMMARY OF THE INVENTION

As a means for achieving the above purpose, the invention as claimed, the sterilizer comprises a power source for generating high voltage, a discharge side electrode to which the high voltage generated by the power source is applied, and a ground side electrode arranged so as to be opposed to the discharge side of the discharge side electrode, in which a packaging material to be sterilized is placed between both electrodes under normal temperature, and is sterilized by applying high voltage pulses in a gas atmosphere, characterized in that the discharge side electrode is provided with unevenness having continuous projections on the discharge side surface of the discharge side electrode.

In the present invention, in the method for sterilizing the packaging material by using the high voltage, the discharge side electrode is provided with unevenness having continuous projections on the discharge side surface thereof, therefore, discharges of strong high voltage pulses are not generated from the tip of the discharge side electrode, but are uniformly generated form the tops of the projections on the outer peripheral surface.

As another means of the method according the present invention, the invention as claimed is characterized in that the unevenness on the surface of the discharge side electrode is formed into a helical form.

In the present invention, strong high voltage pulse discharges are not generated from the tip of the discharge side electrode, but since the electrode has the helical unevenness on the outer peripheral surface, the strong high voltage pulse discharges can be generated from the tops of the helical projections radially and uniformly centering the bar-like discharge side electrode.

As another means of the method according to the present invention, the invention as claimed is characterized in that the packaging material is a container or a film.

In the present invention, as the packaging materials, not only containers such as a PET bottle and a cup but also a plane film can be sterilized by the high voltage pulses.

As another means of the method according to the present invention, the invention as claimed is characterized in that the packaging material is a container and the discharge side electrode is inserted in the container.

In the present invention, the internal surface of the container can be sterilized uniformly without unevenness by inserting the discharge side electrode into the container and generating the high voltage pulse discharges.

As another means of the method according to the present invention, the invention as claimed is characterized in that the gas is at least a kind of gas selected from a group of oxygen, nitrogen, hydrogen, carbon dioxide, air, argon, and helium.

In the present invention, the breakdown voltage can be lowered, and favorable sterilization can be carried out in the plasma generated by the high voltage pulse discharges.

As another means of the method according to the present invention, the invention as claimed is characterized in that at least one kind of gas selected from a group of oxygen, nitrogen, hydrogen, carbon dioxide, air, argon, and helium is introduced during discharge.

In the present invention, the gas can be utilized effectively by introducing the gas during discharge, and further the breakdown voltage can be lowered, and favorable sterilization can be carried out in the plasma generated by the high voltage pulse discharges.

As another means for achieving the above purpose, the invention as claimed, a sterilizer comprises a power source for generating high voltage, a discharge side electrode to which the high voltage generated by the power source is applied, and a ground side electrode arranged so as to be opposed to the discharge side of the discharge side electrode, in which the packaging material to be sterilized is placed between both electrodes under normal temperature and normal pressure, and is sterilized by applying high voltage pulses in a gas atmosphere, characterized in that water or an aqueous solution is given to the packaging material before discharge, during discharge, or before and during discharge.

In the present invention, the method for sterilizing the packaging material by using the high voltage pulse power source is able to improve the sterilization effect because active oxygen or the like is generated by giving water or an aqueous solution to the packaging material before discharge, during discharge or before and during discharge.

As another means of the method according to the present invention, the invention as claimed is characterized in that water or aqueous solution is given to the packaging material so as to cloud the surface of the packaging material.

In the present invention, the sterilization effect is increased by means of letting the particles of, for example, pure water or aqueous solution adhere to the surface of the packaging material in order to cloud the surface of the packaging material made of, for example, a transparent material, and applying the high voltage pulses in this state, and also the surface of the packaging material can be sterilized efficiently and uniformly without unevenness.

As another means of the method according to the present invention, the invention as claimed is characterized in that the gas is at least one kind of gas selected from a group of oxygen, nitrogen, hydrogen, carbon dioxide, air, argon, and helium, and the gas is humidified with the water or aqueous solution and introduced before discharge, during discharge, or before and during discharge.

In the present invention, the gas is humidified with water or an aqueous solution and introduced before discharge, during discharge, or before and during discharge, and is thereby effectively utilized, and moreover, the breakdown voltage can be lowered; the favorable sterilization can be carried out in the plasma generated by the high voltage pulse discharges; and furthermore, the sterilization effect can be improved by giving water or an aqueous solution to the packaging material.

As another means of the method according to the present invention, the invention as claimed is characterized in that the discharge side electrode is provided with unevenness of continuous projections on the discharge side surface of the discharge side electrode.

In the present invention, since the discharge side electrode is provided with the continuous unevenness of the projections on the discharge side surface, strong high voltage pulse discharges are not generated from the tip of the discharge side electrode, but are uniformly generated from the top of the projections on the outer peripheral surface.

As another means of the method according to the present invention, the invention as claimed is characterized in that the unevenness on the discharge side surface is formed into a helical form.

In the present invention, since the outer peripheral surface is provided with helical unevenness thereon, the high voltage pulse discharges are not generated from the tip of the discharge side electrode, but the high voltage pulse discharges can be generated from the tops of the helical form projections uniformly and radially centering the discharge side electrode.

As another means of the method according to the present invention, the invention as claimed is characterized in that the packaging material is a container or a film.

In the present invention, not only containers but also plane films can be sterilized by the high voltage pulses as the packaging materials.

As another means of the method according to the present invention, the invention as claimed is characterized in that the packaging material is a container, and the discharge side electrode is inserted in the container.

In the present invention, it is possible to uniformly sterilize the internal surface of the container with efficiency without unevenness by generating the high voltage pulse discharges with the discharge side electrode inserted in the container.

The invention as claimed for achieving the above purpose comprises a power source for generating high voltage, a discharge side electrode to which the high voltage generated by the power source is applied, and a ground side electrode arranged so as to be opposed to the discharge side of the discharge side electrode, and the device in which the packaging material for sterilization is placed between both electrodes under normal temperature and normal pressure and is sterilized by applying the high voltage pulses in the gas atmosphere is characterized in that the discharge side electrode is provided with the unevenness having continuous projections on the discharge side surface of the discharge side electrode.

In the present invention, since the discharge side electrode is provided with unevenness having continuous projections on the discharge side surface in the device for sterilizing a packaging material by applying the high voltage pulses thereto, the strong high voltage pulse discharges are not generated from the tip of the discharge side electrode, but it is possible to uniformly generate the strong high voltage pulse discharges from the tops of the projections on the outer peripheral surface.

As another means of the device according to the present invention, the invention as claimed is characterized in that the unevenness on the discharge side electrode surface is arranged in a helical structure.

In the present invention, the strong high voltage pulse discharges are not generated from the tip of the discharge side electrode, but since the outer peripheral surface is provided with unevenness in a helical form, the strong high voltage pulse discharges can be generated from the tops of the helical form projections radially and uniformly centering the discharge side electrode.

As another means of the device according to the present invention, the invention as claimed is characterized in that the packaging material placed between the both electrodes is a container or a film.

In the present invention, not only a container or the like but also a plane film can be sterilized as the packaging material by the sterilizer using high voltage pulses.

As another means of the device according to the present invention, the invention as claimed is characterized in that the packaging material is a container, and the sterilizer is provided with a discharge side electrode to be inserted in the container, and a ground side electrode to be arranged along the outer peripheral surface of the container.

In the present invention, the internal surface of the container can be sterilized uniformly with efficiency by inserting the discharge side electrode into the container and generating high voltage pulse discharges across the ground side electrode.

As another means of the sterilizer according to the present invention, the invention as claimed is characterized in that the sterilizer is provided with an introduction means for introducing during discharge at least a kind of gas to be selected from a group of oxygen, nitrogen, hydrogen, carbon dioxide, air, argon, and helium.

In the present invention, since the sterilizer is provided with the introduction means for introducing a kind of gas during discharge, the gas can be introduced easily during discharge and can be used effectively by using the introduction means, and further, the breakdown voltage can be lowered, and the favorable sterilization can be carried out in the plasma generated by the high voltage pulse discharges.

According to the invention as claimed for achieving the above purpose, the device which is provided with a power source for generating high voltage, a discharge side electrode to be applied with the high voltage generated by the power source, and a ground side electrode placed so as to be opposed to the discharge side of the discharge side electrode, in which the packaging material to be sterilized is placed between both electrodes under normal temperature and normal pressure, and is sterilized by applying the high voltage pulses thereto in the gas atmosphere, is characterized in comprising a liquid supply means for giving water or an aqueous solution to the packaging material before discharge, during discharge, or before and during discharge.

In the present invention, since the sterilizer is provided with a liquid supply means for giving water or an aqueous solution to the packaging material before discharge, during discharge, or before and during discharge, the liquid supply means gives water or an aqueous solution to the packaging material, and thereby the sterilization effect by the high voltage pulses can be improved.

As another means of the device according to the present invention, the invention as claimed is characterized in that water or an aqueous solution is given to the surface of the packaging material by the liquid supply means so as to cloud the surface of the packaging material.

In the present invention, for example, particles of pure water or an aqueous solution are made to adhere to the surface of the packaging material by the liquid supply means so as to cloud the surface of the packaging material made of, for example, a transparent material, and the sterilization effect can be improved by applying the high voltage pulses thereto in this state, and also the surface of the packaging material can be sterilized efficiently and uniformly without unevenness.

As another means of the device according to the present invention, the invention as claimed is characterized in that at least a kind of gas selected from a group of oxygen, nitrogen, hydrogen, carbon dioxide, air, argon, and helium is humidified with the water or an aqueous solution and the water or aqueous solution is given to the packaging material before discharge, during discharge, or before and during discharge by the liquid supply means.

In the present invention, the gas can be used effectively by humidifying the gas with water or an aqueous solution and introducing the gas before discharge, during discharge, or before and during discharge, and moreover, the breakdown voltage can be lowered, and the favorable sterilization can be carried out in the plasma generated by the high voltage pulse discharges, and further, the sterilization effect can be improved by giving the water or aqueous solution to the packaging material.

As another means of the device according to the present invention, the invention as claimed is characterized in that the discharge side electrode is provided with unevenness having continuous projections on the discharge side surface thereof.

In the present invention, the discharge side electrode is provided with the unevenness having continuous projections on the discharge side surface. Therefore, it is possible to uniformly generate strong high voltage pulse discharges from the tops of the projections on the outer peripheral surface.

As another means of the device according to the present invention, the invention as claimed is characterized in that the unevenness on the discharge side surface is arranged in a helical structure.

In the present invention, strong high voltage pulses are not discharged from the tip of the discharge side electrode, but since the discharge side electrode is provided with unevenness in a helical structure on the outer peripheral surface, the strong high voltage pulses can be discharged from the tops of the helical form projections radially and uniformly centering the discharge side electrode.

As another means of the device according to the present invention, the invention as claimed is characterized in that the packaging material to be placed between the both electrodes is a container or a film.

In the case of the invention as claimed, not only containers but also plane films can be sterilized by the high voltage pulses as the packaging material.

As another means of the device according to the present invention, the invention as claimed is characterized in that the packaging material is a container, and the device is provided with a discharge side electrode to be inserted in the container, and a ground side electrode arranged along the outer peripheral surface of the container.

In the present invention, strong high voltage pulse discharges are effectively generated from the outer peripheral surface of the discharge side electrode, therefore, the internal surface of the container can be sterilized uniformly with efficiency by inserting the discharge side electrode into the container and generating the high voltage pulse discharges across the ground side electrode.

EXPLANATION OF THE REFERENCES

A1, A2 . . . Sterilizers according to the present invention.
p . . . pitch
1 . . . treating vessel
2 . . . ground side electrode
3 . . . table
4 . . . packaging material (container, film)]
5 . . . discharge side electrode
5A . . . disc type electrode
5a . . . . uneven parts
6 . . . high voltage pulse power source
7 . . . liquid supply means
8 . . . spray member
9 . . . introduction means for gas
10 . . . spray member
11 . . . insulating plate
12 . . . heater
13 . . . disc

DETAILED DESCRIPTION OF THE PREFERRED EMBODIMENTS

Next, preferred embodiments in which the present invention is applied to sterilization of packaging materials (containers, films, or the like) will be explained below referring to the attached drawings.

First Embodiment of the Present Invention

Figure 1:
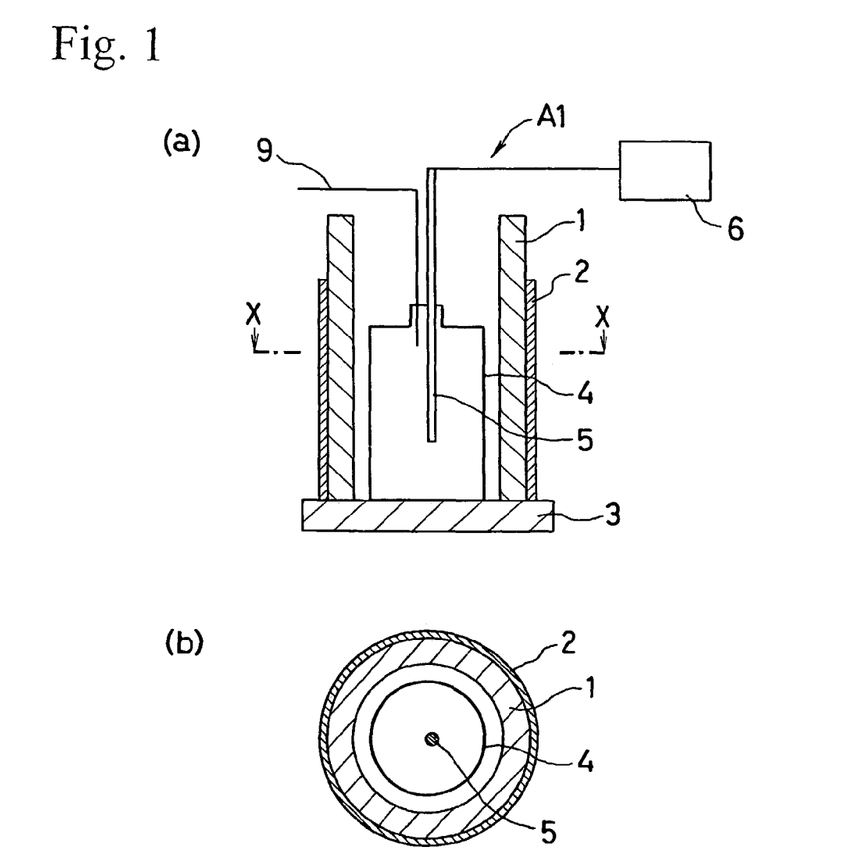
FIG. 1 illustrates an example of an embodiment to which the present invention is applied, where (a) is a schematic view showing the sterilizer according to the present invention by using the high voltage pulse power source, and (b) is a cross section view taken along the line X-X.

FIG. 1(a) is a schematic view showing the sterilizer using the high voltage pulse power source according to the present invention, and FIG. 1(b) is a cross section view taken along the line X-X of the present invention shown in FIG. 1 (a).

Figure 2:
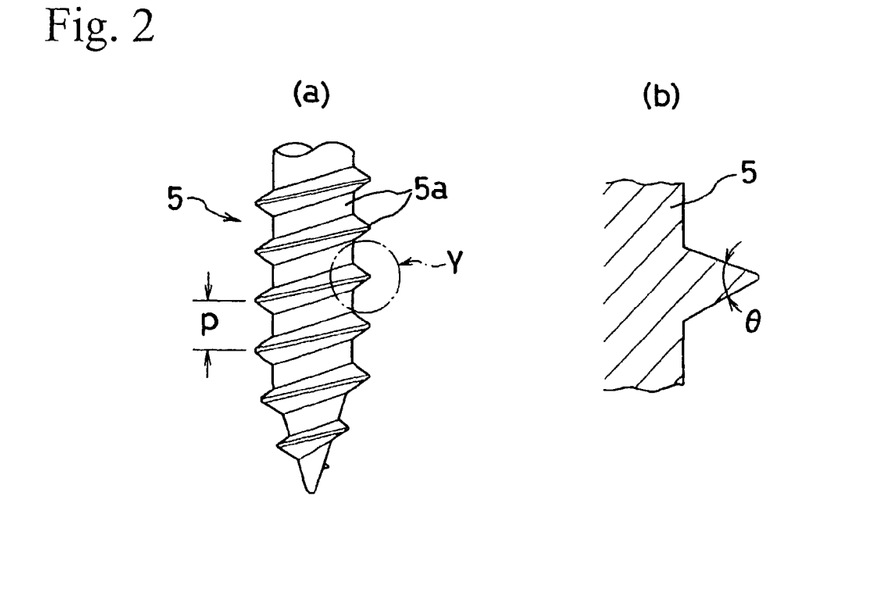
FIG. 2 shows an example of the discharge side electrode embodied according to the present invention, where (a) is an external view of a part of the discharge side electrode, and (b) is a schematic sectional view of the part Y thereof.

FIG. 2 shows an example of the discharge side electrode embodied according to the present invention, where (a) is a sketch drawing of a part of the discharge side electrode, and (b) is an enlarged sectional view of the part Y thereof.

In FIGS. 1(a) and (b), the sterilizer A1 in accordance with the present invention is provided with a pulse power source 6 (corresponding to the power source B shown in the FIG. 9(a)) for generating high pulse voltage, a discharge side electrode 5 for the high pulse voltage generated by the pulse power source 6, a entrance and exit means (not illustrated) for putting the discharge side electrode 5 into and out of the packaging container 4, and the ground side electrode 2 installed by being placed around the outer peripheral surface of a treating vessel 1.

In the sterilizer A1 in accordance with the present invention as shown in FIG. 1(a), the ground side electrode 2 is installed by being placed around the outer peripheral surface of the treating vessel 1, and strong high voltage pulse discharges can be generated uniformly from the tops of the projections of the helical form uneven part 5a on the outer peripheral surface of the discharge side electrode 5.

The treating vessel 1 of the above sterilizer A1 of the present invention is formed cylindrical with thickness not less than 0.1 mm, for example, from acrylic resin, to be large enough to house the packaging container 4. The treating vessel 1 can be formed from a dielectric which is not restricted to acrylic resin but is permitted to those substances for the use such as ceramic, polycarbonate, and polyvinyl chloride. The ground side electrode 2 is formed like a metal plate or a metal net, and is formed cylindrical a little higher than the height of the packaging container 4 so as to cover the whole outer peripheral surface of the packaging container 4. Moreover, the ground side electrode 2 is provided with a terminal for an unshown ground line connection.

The treating vessel 1 of the above sterilizer A1 in accordance with the present invention is installed on a table 3 formed from acrylic resin or the like; the packaging container 4 for the treatment is housed in the treating vessel 1; the discharge side electrode 5 is inserted in the packaging container 4; and the internal surface of the packaging container 4 is sterilization-treated by applying the high voltage pulses to the discharge side electrode 5 from the high voltage pulse power source 6 to generate plasma.

The discharge side electrode 5 has a size permitting to be inserted in the container, and is made of metal such as stainless steel, being formed different from a conventional simple round bar. Namely, as shown in FIG. 2(a), the discharge side electrode 5 is formed with a helical uneven part 5a having continuous projections on the outer peripheral surface, and presents a screw-like form. The pitch p of the uneven part 5a is 0.01 mm to 10 mm, preferably, 0.1 mm to 5 mm, and as shown in FIG. 2(b), the tip angle θ of the projections is 5 degrees to 60 degrees, preferably, 10 degrees to 45 degrees.

When the pitch p is less than 0.01 mm, the intervals of the projections are too narrow and there is a fear of missing uniform discharges, and when the pitch exceeds 10 mm, the number of the projections is reduced and the high voltage pulses are decreased in discharge density. Moreover, when the top angle θ of the projections is less than 5 degrees, the projections are decreased in strength and are prone to be damaged, and on the other hand, when the top angle θ exceeds 60 degrees, strong high voltage pulses become hard to be generated.

The uneven parts 5a of the discharge side electrode 5 may be pointed out at the tops like an ordinary screw, however, the tops are preferred to be not pointed out in order to prevent the strong high voltage pulse discharges from being generated from them. Moreover, on the outer peripheral surface of the electrode with a round bar form, helical projections may be provided afterward by welding or the like.

The uneven parts 5a of the discharge side electrode 5 has only to be unevenness having continuous projections, and the discharge side electrode 5 has not to be formed with helical unevenness 5a on the outer peripheral surface but may be formed with a plurality of unshown projections or needles in order to form unevenness having continuous projections on the outer peripheral surface of the discharge side electrode. Among these arrangements, the helical form unevenness is preferred because it generates uniform discharges.

When sterilizing a packaging container 4 subjected to the treatment by the sterilizer A1 of the present invention using the above high voltage pulse power source 6, it is preferred to sterilize it by applying high voltage pulses to the discharge side electrode 5 in the gas atmosphere without a factor of excessive moisture or the like preventing the uniform and strong high voltage pulses from discharging.

The gases to be used for the present invention are not specially limited, however, at least one kind of gas selected from a group of oxygen, nitrogen, hydrogen, carbon dioxide, air, argon, and helium is preferred for the use because they are capable of lowering the breakdown voltage, and carrying out favorable sterilization in the plasma generated by the high voltage pulses. In the present invention, a mixture of two or more kinds of the above gases can be used in an arbitrary mixing ratio.

Further, at least one kind of gas selected from a group of these oxygen, nitrogen, hydrogen, carbon dioxide, air, argon, and helium can be introduced into the packaging container to be treated before discharge, during discharge, or before and during discharge, however, it is more preferable to introduce the gas therein during discharge because the gasses can effectively be used, and also the breakdown voltage can be lowered, and, further, favorable sterilization can be carried out in the plasma generated by the high voltage pulse discharges.

Figure 4:
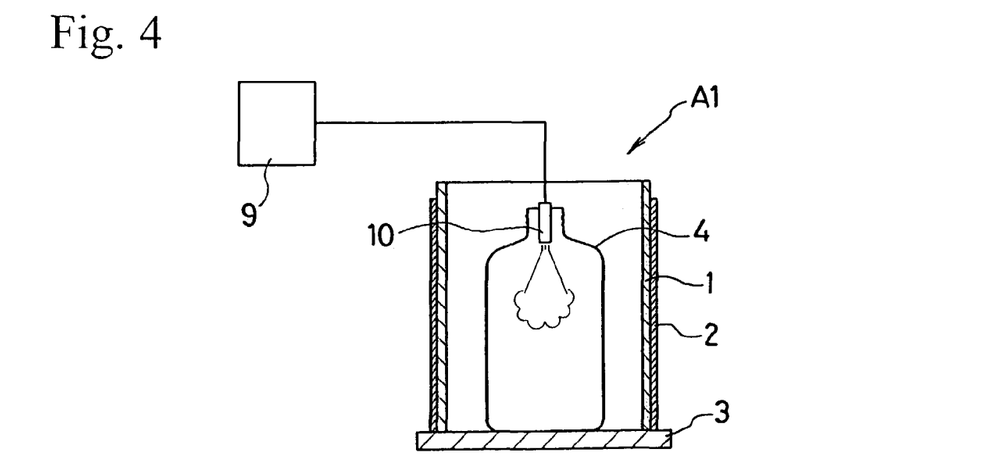
FIG. 4 is a schematic sectional view for explaining the process for blowing a gas to the packaging material.

In order to perform sterilization in the gas atmosphere by applying the high voltage pulses to the discharge side electrode 5, for example, the sterilizer in accordance with the present invention is provided with a gas introduction means 9 as shown in FIG. 4, and a gas mixture containing, for example, 50% or more argon gas is supplied at a rate of 10 liter/min or less from the gas introduction means 9, and is sprayed in the radial direction through a spray member 10 inserted in the upper part of the packaging container 4.

Moreover, when the packaging container 4 such as a PET bottle is in danger of thermal deformation due to a rise in temperature at the time of sterilization by the high voltage pulses, the gases are preferred to be cooled to a suitable temperature for the supply.

After the gas introduction process has been completed by the gas introduction means 9, the discharge side electrode 5 is inserted in the packaging container 4 as shown in FIG. 1, to carry out the sterilization process by applying the high voltage pulses thereto. An insertion amount of the discharge side electrode 5 into the packaging container 4 is not less than $\frac{1}{10}$ of the packaging container 4 in height dimension, preferably, about $\frac{9}{10}$. When the insertion amount of the discharge side electrode 5 is less than $\frac{1}{10}$, a discharge amount into the packaging container 4 becomes insufficient, and when the insertion amount of the discharge side electrode 5 exceeds $\frac{9}{10}$ in height, the bottom of the packaging container 4 is in danger of thermal deformation.

In this sterilization process, for example, a voltage of 38 to 80 kV with a frequency of 100 to 3000 pps is applied, and duration of the high voltage pulse discharges is specified to be 10 sec, for example, in a case of a 500 ml plastic container as the packaging container 4.

Moreover, since the discharge side electrode 5 is formed with helical uneven parts 5a on the outer peripheral surface as described above, the strong high voltage pulse discharges are effectively generated from the tops of the helically continuous projections, and also the high voltage pulse discharges are radially expanded almost over the whole area at 360 degrees centering the discharge side electrode 5.

Therefore, since the sterilization efficiency of the packaging container 4 is substantially improved and also the high voltage pulses are uniformly discharged to the packaging container 4, unevenness of the sterilization can be prevented, and moreover, the packaging container 4 is also prevented from partial thermal deformation.

Second Embodiment of the Present Invention

Figure 3:
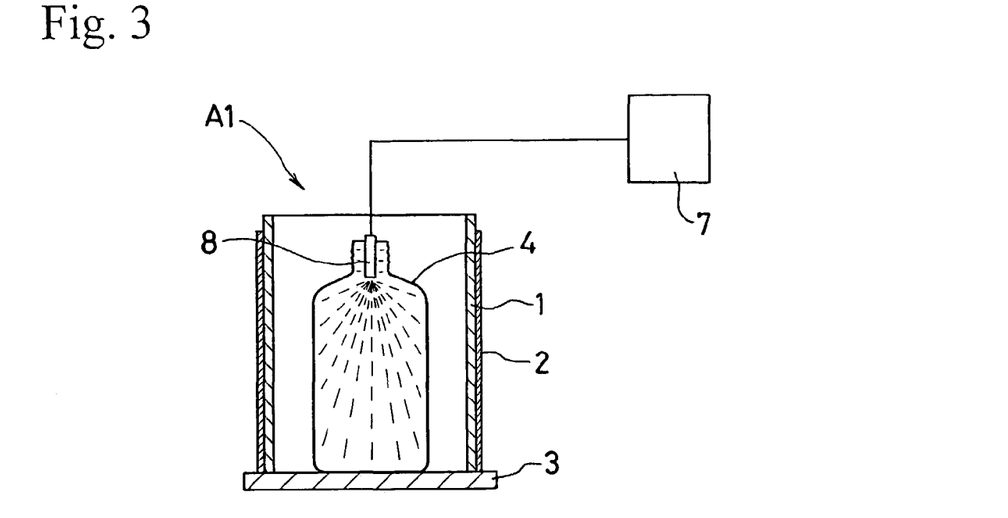
FIG. 3 is a schematic sectional view for explaining the process for giving water or an aqueous solution to the packaging material according to the present invention.

The second embodiment in accordance with the present invention is similar to the first embodiment of the present invention except that a conventional round bar electrode is used as the discharge side electrode 5, and that as shown in FIG. 3, the sterilizer A1 of the present invention is provided with a liquid supply means 7 for giving water or an aqueous solution to the internal surface of the packaging container 4 before discharge.

Moreover, in FIG. 3, the parts similar to those in the first embodiment of the present invention are designated by the same references, and the explanations are omitted here.

In the second embodiment of the present invention, firstly, as shown in FIG. 3, the packaging container 4 is housed in the treating vessel 1, and the process of giving water or an aqueous solution onto the internal surface of this packaging container is carried out. This water-giving process is performed by the liquid supply means 7 and the spraying member 8 for giving water or an aqueous solution. As the spray member 8, a spray, a nebulizer, or the like can be used. As to the water to be given into the packaging container 4, for example, pure water not containing impurities is suitable, and as to the aqueous solution, an organic aqueous solution containing ethanol, acetone, or the like and an inorganic aqueous solution containing electrolytes can be used.

In the above water-giving process, the water or the aqueous solution is fed by pressure from the liquid supply means 7, and is sprayed in the radial directions by the spray member 8 inserted in the upper part of the packaging container, and water particles are made to almost uniformly adhere to over the internal surface of the packaging container 4. When pure water is used, the particle is a few µm in diameter, and in the case of a packaging container 4 such as a plastic container having a capacity of about 500 ml, an amount of the pure water supply is set to 0.01 g to 10 g. In a case of a pure water supply amount exceeding 10 g, the high voltage pulse discharges to be performed later become hard to be generated, and in a case of an amount less than 0.01 g, uniform adhesion of pure water becomes impossible. In appearance, the state in which the pure water particles cloud the whole internal surface of the packaging container 4 shows that the water supply and the amount are proper and are under a favorable condition, and for example, in a case of a transparent packaging container or the like, it is possible to visually observe the state in which the whole internal surface is clouded.

After having completed the water-giving process, as shown in FIG. 1(a), the discharge side electrode 5 is inserted in the packaging container 4, and the sterilization process is carried out by applying the high voltage pulses thereto under the same conditions as described in the first embodiment of the present invention.

According to the present invention, the water particles adhere to the whole internal surface area of the packaging container 4, therefore, the internal surface is uniformly sterilized without uneven plasma generated by the high voltage pulse discharges.

In the second embodiment according to the present invention, an example using a round bar electrode as the discharge side electrode is presented, however, instead of using the round bar electrode in the second embodiment according to the present invention, a discharge side electrode having helical uneven parts 5a on the outer peripheral surface can be adopted as the discharge side electrode 5.

When a discharge side electrode 5 having helical uneven parts 5a on the outer peripheral surface is used along with the water-giving process, strong high voltage pulse discharges are generated with efficiency from the tops of the continuous helical projections as described above, and also the high voltage pulse discharges are radially expanded over the whole 360 degree area centering the discharge side electrode 5. Therefore, a sterilization efficiency of the packaging container 4 is substantially improved and also the high voltage pulse discharges to the packaging container 4 are uniformalized, and as a result, non-uniform sterilization is prevented further.

Third Embodiment of the Present Invention

Figure 6:
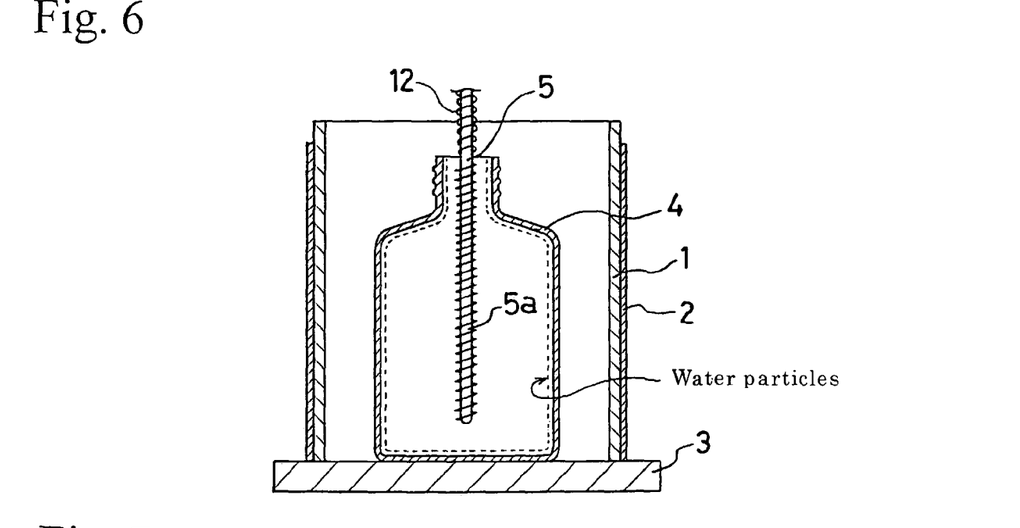
FIG. 6 is a schematic sectional view for explaining the process of inserting the discharge side electrode into the packaging material and sterilizing it with high voltage pulses.

The third embodiment according to the present invention is similar to the first and second embodiments of the present invention except that the first and second embodiments are combined; the sterilizer A1 of the present invention is provided with a gas introduction means 9 and a liquid supply means 7; water or an aqueous solution is fed by pressure from the liquid supply means 7 and is radially sprayed by a spray member 8 inserted in the upper part of the packaging container 4, so that water particles are made to adhere almost uniformly over the internal surface of the packaging container 4; thereafter, a gas mixture containing, for example, 50% or more argon gas is supplied from the gas introduction means 9 at a rate of 10 liters/min or less and sprayed in the radial directions by the spray member 10 inserted in the upper part of the packaging container 4, to purge superfluous moisture floating in the packaging container 4; the discharge side electrode 5 is inserted in the packaging container 4 as shown in FIG. 6; and thus the sterilization process is carried out by applying the high voltage pulses thereto under almost the same conditions as described in the first embodiment of the present invention.

Moreover, in such a case as moisture adheres to the surface of the discharge side electrode 5 and favorable high voltage pulse discharges cannot be performed, it is preferred to remove the moisture, and for example, the moisture is removed by detecting it by an unshown sensor, energizing a heater 12 installed on the upper part of the discharge side electrode 5 as shown in FIG. 6, and properly heating the discharge side electrode to vaporize the moisture on the surface.

According to the third embodiment of the present invention, water particles adhere to the internal surface of the packaging container 4, therefore, the sterilization effect is improved in the plasma generated by the high voltage pulse discharges, and moreover, since gas is introduced into the packaging container, the breakdown voltage can be lowered, and the sterilization efficiency of the packaging container is substantially improved in the plasma generated by the high voltage pulse discharges.

Fourth Embodiment of the Present Invention

The fourth embodiment of the present invention is similar to the first, second, and third embodiments of the present invention except that the water-giving process and the process for blowing gas are not performed into dividually but performed simultaneously.

Figure 5:
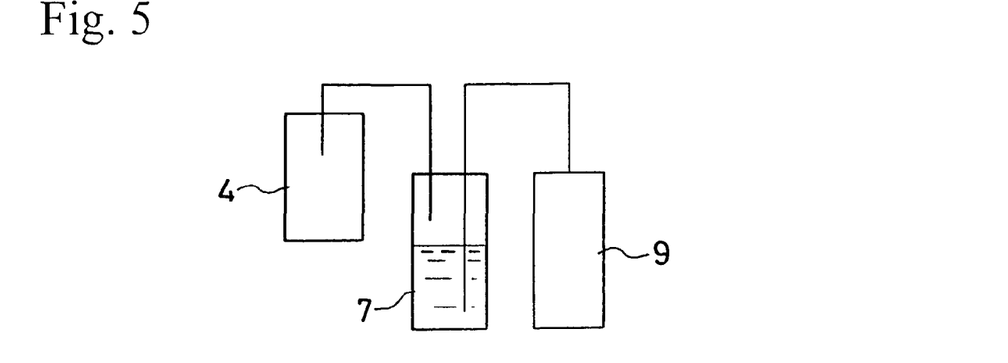
FIG. 5 is a drawing for explaining the bubbling process of giving water or an aqueous solution and blowing a gas at the same time.

Moreover, in FIG. 5, the parts similar to those in the first to third embodiments of the present invention are designated by the same reference numerals, and the explanation therefor is omitted here.

For example, as shown in FIG. 5, moisture and gas are supplied at the same time by feeding a gas from the gas introduction means 9 into the liquid supply means 7 to humidify it by bubbling herein, and then supplying the gas into the packaging container 4 to be treated. The supply of the moisture and the gas by the bubbling is performed at the same time before and during discharge. Moreover, the adhesion of water to the internal surface of the packaging container 4 to be treated and the substitution with the air in the packaging container are performed. Then, a gas feeding amount before discharge is controlled so as to be more than that during discharge. For this purpose, the gas introduction means 9 is arranged so as to be variable in capability. Moreover, before discharge, the discharge side electrode is placed outside of the packaging container 4 to be treated, and during discharge, it is placed inside of the packaging container 4 to be treated. For this purpose, before discharge, a gas substitution rate in the packaging container 4 to be treated is increased, and also water is made to adhere to the internal surface of this packaging container while water is prevented from adhering to the discharge side electrode, and during discharge, a gas feeding amount is decreased to replenish the packaging container 4 for treatment with the gas and generate discharges with efficiency, and also the adhesion of water to the discharge side electrode in the packaging container for treatment is suppressed.

In addition, in the fourth embodiment of the present invention, water is given to the internal surface of the packaging container 4 and a gas is introduced into the packaging container 4, therefore, just as the case of the third embodiment of the present invention, a sterilization efficiency of the packaging container is substantially improved, and also the high voltage pulses are uniformly discharged to the packaging container 4, and thus, unevenness of the sterilization is prevented.

Fifth Embodiment of the Present Invention

The fifth embodiment of the present invention is similar to the first, second, third, and fourth embodiments of the present invention except that a film is used as a packaging material 4.

Figure 7:
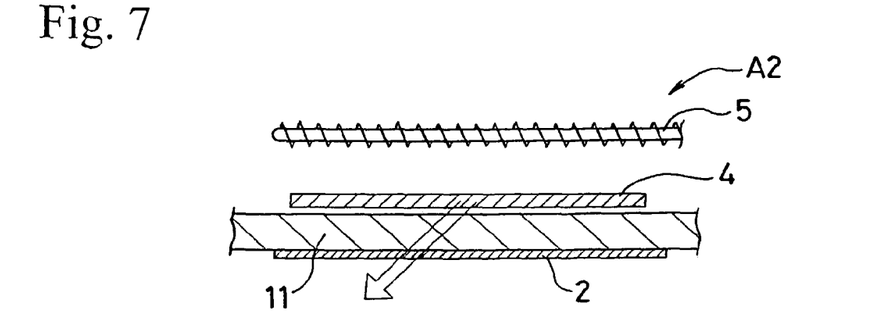
FIG. 7 is an explanatory cross section view showing an example of an embodiment in which the present invention is applied to sterilization of a film.

FIG. 7 is an explanatory cross section view showing an example of the embodiment applying the present invention to the sterilization of a film.

Moreover, in FIG. 7, the parts similar to those in the first through fourth embodiments of the present invention are designated by the same reference numerals, and the explanation is omitted here.

In FIG. 7, the sterilizer A2 according to the present invention comprises an unshown pulse power source for generating a high pulse voltage, a discharge side electrode 5 provided with unevenness (helical unevenness) having continuous projections to be applied with the high pulse voltage generated by the pulse power source, a packaging material (film) 4 for a treatment of sterilization by the high voltage pulses, an insulating plate 11 formed of a dielectric such as acrylic resin, ceramics, polycarbonate, polyvinyl chloride placed under the packaging material 4, and a ground side electrode 2 placed under the insulating plate 11 so as to be opposed to the discharge side of the discharge side electrode 5.

The ground side electrode 2 is formed of a metal such as stainless steel a little wider than the width of the packaging material 4. The ground side electrode 2 is provided with an unshown terminal for ground line connection. The discharge side electrode 5 may be provided with a plurality of terminals.

As shown in FIG. 7, the top surface (the surface to be in contact with packaging goods) of the packaging material 4 is treated by sterilization under almost the same conditions described in the first embodiment of the present invention, by placing the packaging material 4 subjected to sterilization between both electrodes under normal temperature and normal pressure, and generating plasma by applying the high voltage pulses from an unshown high voltage pulse power source while moving the packaging material 4 by a moving means in the gas atmosphere. After the top surface has been treated by sterilization, it is preferable to sterilize the whole packaging material 4 by treating the bottom surface of the packaging material 4 by sterilization in the same way as the top surface is treated by sterilization continuously or discontinuously, and this way of treatment is specially preferable in such a case as the packaging material 4 is used for packaging foods.

The sterilization treatment of the packaging material 4 under almost the same conditions as described in the first embodiment according to the present invention, by feeding water or an aqueous solution by pressure from an unshown liquid supply means; spraying it over the top surface of the packaging material 4; letting water particles almost uniformly adhere to all over the top surface of the packaging material 4; placing between both electrodes the packaging material 4, which is given water particles and is subjected to sterilization, under normal temperature and normal pressure; and generating plasma by applying the high voltage pulses from the unshown high voltage pulse power source while moving the packaging material 4 in a gas atmosphere by the moving means, is able to make an improvement on the sterilization effect, therefore, this sterilization treatment is preferable.

When the discharge side electrode 5 having helical uneven parts on the outer peripheral surface is used along with the water-giving process, uniform high voltage pulse discharges are generated from the tops of the helically continuous uneven parts and expanded radially onto the top surface of the packaging material 4 as described above, therefore, the sterilization efficiency of the packaging material 4 is substantially improved further.

Moreover, the descriptions of the above embodiments are for explaining the present invention, and is not to limit the inventions as claimed in the appended claims, nor to reduce the scope thereof. Further, the compositions of each part of the present invention are not to be restricted to those of the above embodiments, but various modifications are possible within the technical range as claimed in the appended claims.

In the descriptions of the above embodiments, the use of the treating vessel 1 is mentioned as an example, however, it is not always necessary to use the treating vessel 1. Moreover, the forms of the treating vessel 1 and the ground side electrode 2 are not particularly limited, but they may be polygonal, or similar figure to the packaging material to be treated.

EMBODIMENTS

Next, the present invention will be explained in specific examples below, however, the present invention is not to be limited to these examples insofar as not departing from the spirit and scope of the claimed invention.

Embodiment 1

(Preparation of Bacteria Adhesion Packaging Container for Sterilization Test)

A predetermined quantity of spores of *Bucillus subtilis, B. cereus,* or *Asperillus niger* are made to uniformly adhere to the internal surface of a 500 ml plastic container, and this is adopted as a bacteria adhesion packaging container for testing sterilization.

The above bacteria adhesion packaging container for sterilization test is placed at a predetermined position of the sterilizer in accordance with the present invention as illustrated in FIG. 1, and high voltage pulses were applied thereto. The discharge side electrode used is a disc type electrode made of SUS (having a 15 mm disc diameter, and a 30 mm pitch of discs) as illustrated in FIG. 8, and the discharge conditions are 45 kV, 400 Hz, and 10 seconds.

Figure 8:
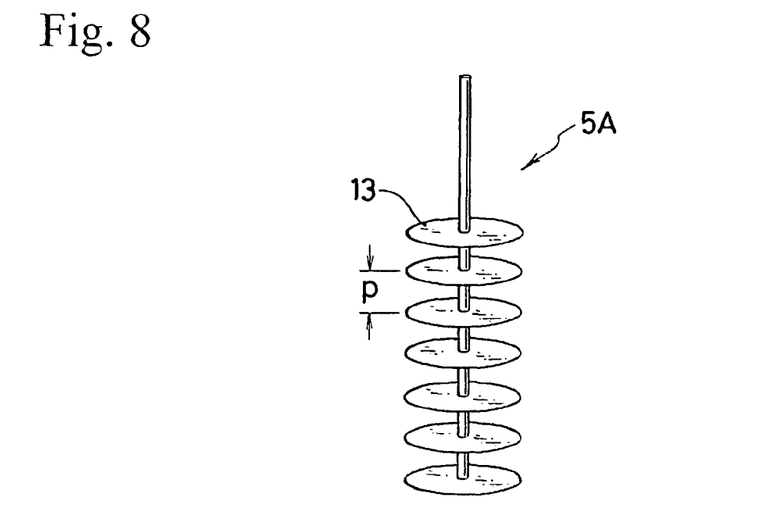
FIG. 8 is an explanatory drawing for explaining another embodiment of the discharge side electrode according to the present invention.

The disc type electrode 5A shown in FIG. 8 is provided with a plurality of discs 13 arranged in parallel at a pitch p.

(Incubation Method)

Immediately after the discharges were ended, a nitrogen gas was introduced into the bacteria adhesion packaging container, and purged the container of the impurities which might be remaining therein (5l/min, 30 seconds). Thereafter, a tripto-soya-bouillon culture medium of 30 ml was poured into the container immediately, and was fully shaken with a sterilized cap on the container before incubating the bacteria under the following conditions.

(Conditions for Incubation)

After having incubated *Batillus subtillis, B. cereus* at 35° C. for 10 days, and *Aspergillus niger* at 25° C. for 10 days, a sterilization effect value D [Sterilization effect value D=−log (Number of survived bacteria/Number of initial bacteria) was calculated. The results of the sterilization effect value D are shown in Table 1 together with a water adhesion amount, an adhesion method, a discharge side electrode used, a kind of gas introduced, a gas flow rate, or the like.

Embodiment 2

The sterilization effect was tested in the same way as in the embodiment 1 except that a helical form electrode 5 of stainless (SUS) was used as the discharge side electrode as shown in FIG. 2, and the results are shown in the Table 1.

Embodiment 3

The test was carried out in the same way as in the Embodiment 2 except that an argon gas substituted for the inside of the container before electrical discharge, and then electricity was discharged while feeding the gas therein at 3 liters/min, and the results are shown in the Table 1.

Embodiment 4

The test was carried out in the same way as in the Embodiment 1 except that using the sterilizer shown in FIG. 3, water was sprayed (3 g/container) in the container before the electrical discharge, and a 10 mm diameter round bar electrode of stainless steel (SUS) was used as the discharge side electrode, and the results are shown in the Table 1.

Embodiment 5

The test was carried out in the same way as in the Embodiment 1 except that using the sterilizer shown in FIG. 5, water was made to adhere (approximately 1 g/container) to the inside of the container to the extent to cloud the container before the electric discharge, and the results are shown in the Table 1.

Embodiment 6

The test was carried out in the same way as in the Embodiment 5 except that a gas mixture of 70% argon and 30% nitrogen was fed at 3 liters/min during the electric discharge, and the results are shown in the Table 1.

Embodiment 7

The test was carried out in the same way as in the Embodiment 6 except that the discharge side electrode was a disc type electrode used in the Embodiment 1, and the results are shown in Table 1.

Embodiment 8

Using the sterilizer as shown in FIG. 5 and FIG. 6, electricity was discharged while feeding the humidified gas mixture of 70% argon and 30% nitrogen at 3 liters/min before and during the electric discharge. The test was carried out using the helical electrode of SUS as the discharge side electrode, and the others are the same as those in the Embodiment 1, and the results are shown in the Table 1.

|  | Water adhesion | | Discharge side electrode | Gas introduced | | Sterilization effect value D | | |
| --- | --- | --- | --- | --- | --- | --- | --- | --- |
|  | Amount (g) | Method |  | Kind of gas | flow rate(l/min) | *B. subtillis* | *B. cereus* | *A. niger* |
| Embodiment 1 | None | — | disk type | Air | — | 2.1 | 2.1 | 2.3 |
| Embodiment 2 | None | — | helical | Air | — | 2.3 | 2.2 | 2.5 |
| Embodiment 3 | None | — | helical | Argon | 3 | 2.8 | 2.7 | 3.0 |
| Embodiment 4 | 3 | spray | round bar | Air | — | 2.2 | 2.2 | 3.0 |
| Embodiment 5 | abt. 1 g (cloud) | bubbling | round bar | Air | — | 3.5 | 3.7 | 4.0 |
| Embodiment 6 | abt. 1 g (cloud) | bubbling | round bar | Ar: 70% N: 30% | 3 | 4.3 | 4.3 | 4.9 |
| Embodiment 7 | abt. 1 g (cloud) | bubbling | disk type | Ar: 70% N: 30% | 3 | 4.9 | 5.2 | 6.0 |
| Embodiment 8 | (cloud) | bubbling | helical | Ar: 70% N: 30% | 3 | 5.8 | 6.0 | 6.9 |

According to the sterilization method as claimed in the present invention, comprising a power source for generating high voltage, a discharge side electrode to which the high voltage generated by the power source is applied, and a ground side electrode placed so as to be opposed to the discharge side of the discharge side electrode; in which a packaging material to be sterilized is placed between both electrodes under normal temperature and normal pressure, and is sterilized by applying the high voltage pulses in a gas atmosphere, the discharge side electrode is provided with unevenness having continuous projections on the discharge side surface, therefore, the method has a remarkable effect that strong high voltage pulse discharges are not generated from the tip of the discharge side electrode, but can be generated uniformly from the tops of the uneven parts on the outer peripheral surface. Thus, the method is able to improve the sterilization effect of the packaging materials for packaging articles to be packed such as liquids, solids, or a combination of both which are foods, medical supplies, Chinese medicines, cosmetics, feeds, fertilizer, or the like, especially packaging materials for packaging foods.

According to the sterilization method as claimed in the present invention, the sterilization method as claimed has another remarkable effect that since the discharge side electrode is provided with helical unevenness on the outer peripheral surface, the strong high voltage pulse discharges are not generated from the tip of the discharge side electrode, but can be generated uniformly from the tops of the helical projections centering the discharge side electrode, and thus, the method is able to improve the sterilization effect and prevent non-uniformity of the sterilization.

According to the sterilization method as claimed in the present invention, the packaging material is a container or a film in the sterilization method as claimed. Therefore, the method has another remarkable effect of being able to sterilize not only containers such as PET bottles and cups, but also plane films by the high voltage pulses.

According to the sterilization method as claimed in the present invention, the packaging material is a container and the discharge side electrode is inserted in the container in the sterilization method as claimed. Therefore, the method has another remarkable effect of being able to uniformly and efficiently sterilize the internal surface of the container without unevenness by generating the high voltage pulse discharges.

According to the sterilization method claimed as in the present invention, the gas is at least one kind of gas to be selected from a group of oxygen, nitrogen, hydrogen, carbon dioxide, air, argon, and helium, in the sterilization method as claimed. Therefore, the method has further remarkable effects of being able to decrease the breakdown voltage and perform favorable sterilization in the plasma generated by the high voltage pulse discharges.

According to the sterilization method claimed as in the present invention, at least one kind of gas selected from a group of oxygen, nitrogen, hydrogen, carbon dioxide, air, argon, and helium is introduced during discharge in the method claimed. Therefore, the method has further remarkable effects of being able to make effective use of the gas, also to lower the breakdown voltage, and to perform favorable sterilization in the plasma generated by the high voltage pulse discharges.

According to the sterilization method claimed as in the present invention, water or an aqueous solution is given to the packaging material before discharge, during discharge, or before and during discharge to produce active oxygen in the method in which the sterilizer is provided with a power source for generating high voltage, a discharge side electrode to which the high voltage generated by the power source is applied, and a ground side electrode placed so as to be opposed to the discharge side of the discharge side electrode; in which a packaging material to be sterilized is placed between both electrodes under normal temperature and normal pressure, and is sterilized by applying the high voltage pulses in a gas atmosphere, therefore, the method has another remarkable effect of being able to improve the sterilization effect of the packaging material for packaging articles to be packaged as liquids, solids, and a combination thereof such as foods, medical supplies, Chinese medicines, cosmetics, feeds, and fertilizers, especially packaging materials for packaging foods.

According to the sterilization method claimed as in the present invention, the water or aqueous solution is given so as to cloud the surface of the packaging material in the sterilization method as claimed. Therefore, the method has further remarkable effects of being able to improve the sterilization effect by letting particles of, for example, pure water or aqueous solution adhere to the surface of the packaging material so that, for example, the surface of a packaging material formed of a transparent material is clouded, and applying the high voltage pulses thereto in this state, and also being able to uniformly sterilize the surface of the packaging material with efficiency without unevenness.

According to the sterilization method claimed as in the present invention, in the sterilization method as claimed, the gas is at least one kind of gas selected from a group of oxygen, nitrogen, hydrogen, carbon dioxide, air, argon, and helium, and the gas is humidified with the water or aqueous solution and introduced before discharge, during discharge, or before and during discharge. Therefore, the method has further remarkable effects that the gas can be used effectively; the breakdown voltage can be lowered; favorable sterilization can be performed into the plasma generated by the high voltage pulse discharges; and further, the sterilization effect can be improved by giving the water or aqueous solution to the packaging material.

According to the sterilization method claimed as in the present invention, in the sterilization method as claimed, the discharge side electrode is provided with unevenness having continuous projections on the discharge side surface. Therefore, the method has another remarkable effect that strong high voltage pulse discharges can be generated uniformly from the tops of the projections and uneven sterilization can be prevented.

According to the sterilization method claimed as in the present invention, in the sterilization method as claimed, the unevenness on the discharge side surface is formed into to a helical structure. Therefore, the method has another remarkable effect that strong high voltage pulse discharges are not generated from the tip of the discharge side electrode, but the strong high voltage pulse discharges are uniformly generated from the tops of the helical projections radially centering the discharge side electrode, and thus, the sterilization effect can be improved and uneven sterilization can be eliminated.

According to the sterilization method claimed as in the present invention, in the sterilization method as claimed, the packaging material is a container of a film. Therefore, the method has another remarkable effect of being able to sterilizing not only containers but also plane films.

According to the sterilization method claimed as in the present invention, in the sterilization method as claimed, the packaging material is a container and the discharge side electrode is inserted in the container. Therefore, the method has another effect of being able to uniformly sterilize the internal surface of the container with efficiency without unevenness.

According to the sterilizer claimed as in the present invention, in the sterilizer which is provided with a power source for generating high voltage, a discharge side electrode to which the high voltage generated by the power source is applied, and a ground side electrode placed so as to be opposed to the discharge side of the discharge side electrode; in which a packaging material to be sterilized is placed between both electrodes under normal temperature and normal pressure, and is sterilized by applying the high voltage pulses in a gas atmosphere, the discharge side electrode is provided with unevenness having continuous projections on the discharge side surface. Therefore, the method has a remarkable effect that strong high voltage pulse discharges are not generated from the tip of the discharge side electrode, but can uniformly be generated from the tops of the uneven parts on the outer peripheral surface, and thus, the method is able to improve the sterilization effect of the packaging materials for packaging articles to be packed such as liquids, solids, or a combination of both which are foods, medical supplies, Chinese medicines, cosmetics, feeds, fertilizer, or the like, especially packaging materials for packaging foods.

According to the sterilizer claimed as in the present invention, in the sterilizer as claimed, the unevenness on the discharge side electrode surface is arranged in a helical structure. Therefore, the sterilizer has another remarkable effect that strong high voltage pulse discharges are not generated from the tip of the discharge side electrode, but the strong high voltage pulse discharges can be generated from the tops of the helical uneven parts uniformly and radially centering the discharge side electrode, and this improves the sterilization effect and eliminates non-uniformity of sterilization.

According to the sterilizer claimed as in the present invention, in the sterilizer as claimed, the packaging material placed between the both electrodes is a container or a film. Therefore, the sterilizer has another remarkable effect that not only containers but also plane films can be sterilized by the sterilizer using the high voltage pulses.

According to the sterilizer claimed as in the present invention, in the sterilizer as claimed, the packaging material is a container, and the sterilizer is provided with the discharge side electrode to be inserted in this container, and the ground side electrode arranged along the outer periphery of the container, and strong high voltage pulse discharges are effectively generated from the outer peripheral surface of the discharge side electrode. Therefore, the sterilizer has another remarkable effect of being able to uniformly sterilize the internal surface of the container with efficiency by inserting the discharge side electrode in the container, and generating the high voltage pulse discharges across the ground side electrode.

According to the sterilizer claimed as in the present invention, in the sterilizer as claimed, the sterilizer is provided with an introduction means for introducing at least one kind of gas selected from a group of oxygen, nitrogen, hydrogen, carbon dioxide, air, argon, and helium during discharge, therefore, the sterilizer has further remarkable effects that the gas can be introduced with ease during discharge by using this introduction means and can be used effectively, and moreover, the breakdown voltage is lowered, and favorable sterilization can be can be carried out in the plasma generated by the high voltage pulse discharges.

According to the sterilizer claimed as in the present invention, the sterilizer which is provided with a power source for generating high voltage, a discharge side electrode to which the high voltage generated by the power source is applied, and a ground side electrode placed so as to be opposed to the discharge side of the discharge side electrode; in which a packaging material to be sterilized is placed between both electrodes under normal temperature and normal pressure, and is sterilized by applying the high voltage pulses in a gas atmosphere, is provided with a liquid supply means for giving water or an aqueous solution to the packaging material before discharge, during discharge, or before and during discharge, therefore, the sterilizer has a remarkable effect that strong high voltage pulse discharges are effectively generated from the outer peripheral surface of the discharge side electrode by giving the water or aqueous solution to the packaging material by this liquid supply means, and thus, the sterilizer is able to improve the sterilization effect of the packaging materials for packaging articles to be packed such as liquids, solids, or a combination of both which are foods, medical supplies, Chinese medicines, cosmetics, feeds, fertilizer, or the like, especially packaging materials for packaging foods.

According to the sterilizer claimed as in the present invention, in the sterilizer as claimed, said liquid supply means gives water or an aqueous solution to the packaging material so as to cloud the surface thereof. Therefore, the sterilizer has further remarkable effects that the sterilization effect can be improved by making, for example, particles of pure water or aqueous solution adhere to the surface of the packaging material by the liquid supply means so that the surface of the packaging material made of, for example, a transparent material is clouded, and applying the high voltage pulses in this state, and also the surface of the packaging material can be sterilized uniformly with efficiency and further, moisture does not remain on the surface of the packaging material after sterilization.

According to the sterilizer claimed as in the present invention, in the sterilizer as claimed, at least one kind of gas selected from a group of oxygen, nitrogen, hydrogen, carbon dioxide, air, argon, and helium is humidified with said water or aqueous solution and the liquid supply means gives the water or aqueous solution to the packaging material before discharge, during discharge, or before and during discharge. Therefore, the sterilizer has further remarkable effects that the gas can effectively be used; the breakdown voltage can be lowered; favorable sterilization can be carried out in the plasma generated by the high voltage pulse discharges; and the sterilization effect can be improved by giving the water or aqueous solution to the packaging material.

According to the sterilizer claimed as in the present invention, in the sterilizer as claimed, the discharge side electrode is provided with unevenness having continuous projections on the discharge side surface. Therefore, the sterilizer has another remarkable effect of being able to generate uniform strong high voltage pulse discharges from the tops of the projections on the outer peripheral surface, and thereby improving the sterilization effect.

According to the sterilizer claimed as in the present invention, in the sterilizer as claimed, the unevenness on the discharge side surface is arranged in a helical structure and strong high voltage pulse discharges are not generated from the tip of the discharge side electrode, but the discharge side electrode has unevenness of a helical structure on the outer peripheral surface. Therefore, the sterilizer has further remarkable effects of being able to generate the strong high voltage pulse discharges from the tops of the projections of said helical structure radially and uniformly centering the discharge side electrode, and improve the sterilization effect and eliminate non-uniformity of sterilization.

According to the sterilizer claimed as in the present invention, in the sterilizer as claimed, the packaging material placed between both electrodes is a container or a film. Therefore, the sterilizer has another remarkable effect of being able to sterilize not only containers, and also plane films.

According to the sterilizer claimed as in the present invention, in the sterilizer as claimed, said packaging material is a container, and the sterilizer is provided with a discharge side electrode to be inserted in this container, and a ground side electrode arranged along the outer peripheral surface of the container, so strong high voltage pulse discharges are effectively generated from the outer peripheral surface of the discharge side electrode. Therefore, the sterilizer has another remarkable effect of being able to uniformly sterilize the internal surface of the container with efficiency by inserting the discharge side electrode into the container and generating the high voltage pulse discharges across the ground side electrode.

What is claimed is:

1. A method for sterilizing a surface of a packaging material by using a high voltage pulse power source, comprising a power source for generating high voltage, a high voltage electrode to which the high voltage generated by said power source is applied, and a ground side electrode arranged so as to be opposed to the discharge side of the high voltage electrode, in which the packaging material to be sterilized is placed between both electrodes under normal temperature and normal pressure, and is sterilized by applying high voltage pulses in a gas atmosphere, characterized in that the surface of the packaging material to be sterilized is placed so as to be opposed to the discharge side of the high voltage electrode, and water or an aqueous solution is disposed onto said surface of the packaging material to be sterilized before discharge.

2. The sterilization method as claimed in claim 1, characterized in that said water or aqueous solution is given to said packaging material so as to cloud the surface of said packaging material.

3. The sterilization method as claimed in claim 1, characterized in that said gas is at least one kind of gas selected from a group of oxygen, nitrogen, hydrogen, carbon dioxide, air, argon, and helium, and the gas is humidified with said water or aqueous solution and introduced before discharge.

4. The sterilization method as claimed in claim 1, characterized in that said high voltage electrode is provided with unevenness having continuous projections on the discharge side surface of said high voltage electrode.

5. The sterilization method as claimed in claim 4, characterized in that said unevenness on the discharge side surface is formed into a helical form.

6. The sterilization method as claimed in claim 1, characterized in that said packaging material is a container or a film.

7. The sterilization method as claimed in claim 1, characterized in that said packaging material is a container, and the high voltage electrode is inserted in the container.

8. The sterilization method as claimed in claim 2, characterized in that said gas is at least one kind of gas selected from a group of oxygen, nitrogen, hydrogen, carbon dioxide, air, argon, and helium, and the gas is humidified with said water or aqueous solution and introduced before discharge.

9. The sterilization method as claimed in claim 8, characterized in that:

said high voltage electrode is provided with unevenness having continuous projections on the discharge side surface of said high voltage electrode;

said unevenness on the discharge side surface is formed into a helical form;

said packaging material is a container or a film;

said packaging material is a container, and the high voltage electrode is inserted in the container.

* * * * *

UNITED STATES PATENT AND TRADEMARK OFFICE
CERTIFICATE OF CORRECTION

PATENT NO.         : 7,425,300 B2
APPLICATION NO.    : 10/601007
DATED              : September 16, 2008
INVENTOR(S)        : Satoshi Masaoka et al.

It is certified that error appears in the above-identified patent and that said Letters Patent is hereby corrected as shown below:

Title page, (54) Title, "METHOD FOR STERILIZING PACKAGING MATERIAL BY USING HIGH VOLTAGE PULSE POWER SOURCE" should read --METHOD FOR STERILIZING PACKAGING MATERIAL BY USING HIGH VOLTAGE PULSE POWER SOURCE AND A DEVICE THEREFOR--;

Title page, (74) Attorney, Agent, or Firm, "Lebovivi" should read --Lebovici--;

Column 1, line 3, "PULSE POWER SOURCE" should read --PULSE POWER SOURCE AND A DEVICE THEREFOR--;

Column 1, line 50, "the system" should read --to the system--;

Column 1, line 60, "9-(a)" should read --9a--;

Column 1, line 64, "a entrance" should read --an entrance--;

Column 2, line 66, "form" should read --from--;

Column 3, line 1, "according the" should read --according to the--;

Column 8, line 24, "a entrance" should read --an entrance--;

Column 12, line 21, "dividually" should read --individually--;

Column 14, line 1, "inventions" should read --invention--;

Column 18, line 11, "into to a" should read --into a--;

Column 18, lines 22-23, "sterilizing" should read --sterilize--; and

UNITED STATES PATENT AND TRADEMARK OFFICE
CERTIFICATE OF CORRECTION

PATENT NO. : 7,425,300 B2
APPLICATION NO. : 10/601007
DATED : September 16, 2008
INVENTOR(S) : Satoshi Masaoka et al.

It is certified that error appears in the above-identified patent and that said Letters Patent is hereby corrected as shown below:

Column 19, line 23, "be can be carried" should read --be carried--.

Signed and Sealed this

Seventh Day of July, 2009

JOHN DOLL
*Acting Director of the United States Patent and Trademark Office*